United States Patent [19]

Carollo et al.

[11] Patent Number: 4,587,555

[45] Date of Patent: May 6, 1986

[54] NEUTRON AND X-RAY RADIATION COMBINED INSPECTION MEANS AND METHOD

[75] Inventors: Sammy F. Carollo, Irving; William E. Dance, Dallas, both of Tex.

[73] Assignee: LTV Aerospace and Defense Co., Dallas, Tex.

[21] Appl. No.: 557,035

[22] Filed: Dec. 1, 1983

Related U.S. Application Data

[63] Continuation-in-part of Ser. No. 324,519, Nov. 24, 1981.

[51] Int. Cl.$^4$ .................................................. H04M 5/32
[52] U.S. Cl. ...................................... 358/111; 378/99; 250/353; 250/390
[58] Field of Search ......................... 358/111; 378/99; 250/358.1, 390, 391, 392, 393, 483.1

[56] References Cited

U.S. PATENT DOCUMENTS

| | | | |
|---|---|---|---|
| 2,297,478 | 9/1942 | Kallmann et al. | 250/390 J |
| 2,344,042 | 3/1944 | Kallmann et al. | 250/390 J |
| 3,786,253 | 1/1974 | Haffner et al. | 250/390 J |
| 3,887,807 | 6/1975 | Poignant, Jr. et al. | 378/28 |
| 3,889,112 | 6/1975 | Holmes et al. | 250/255 |
| 3,891,852 | 6/1975 | Bollen et al. | 358/483.1 |
| 3,988,586 | 10/1976 | Stuart et al. | 350/390 |
| 4,124,799 | 11/1978 | Schittenhelm | 378/18 |
| 4,152,598 | 5/1979 | Stewart | 250/391 |

*Primary Examiner*—Howard W. Britton
*Assistant Examiner*—Edward L. Coles

*Attorney, Agent, or Firm*—J. M. Cate; S. S. Sadacca

[57] ABSTRACT

A radiographic imaging system (10) includes first and second housing segments (10a, 10b) with the second housing segment (11b) having a low-light-sensitivity television camera (13) mounted therein. The first housing segment (11a) has a radioluminescent screen structure (20) fitted within an opening (16). A workpiece (24) is positioned adjacent the radioluminescent screen (20) and between the screen and a source of radiation (25a, 25b). The screen structure includes means for producing a scintillation shadowgraph pattern in response to impingement on the screen of radiation directed through the object. The camera (13) has its optical input section directed toward the radioluminescent screen for receiving the scintillation shadowgraph pattern and has a target means for forming charge patterns corresponding to the scintillation patterns produced on the radioluminescent screen and scanning means for scanning the target means to generate an optical signal corresponding to the charge pattern formed on the target. Both a source of neutron radiation and X-ray is used to produce a shadowgraph pattern on the radioluminescent screen in response to impingement on the screen structure of radiation directed through the object. Signals derived from sequential scans of the target are processed and the signals generated as a result of the exposure of the object to radiation from the neutron radiation source and exposure of the object to radiation from the X-ray source are combined to produced a television display corresponding to the combination of the signals.

21 Claims, 5 Drawing Figures

NEUTRON AND X-RAY RADIATION COMBINED INSPECTION MEANS AND METHOD

CROSS REFERENCE TO RELATED APPLICATION

The present application is a continuation-in-part application of United States patent application Ser. No. 324,519, filed Nov. 24, 1981, for RADIOGRAPHIC INSPECTION MEANS AND METHOD.

TECHNICAL FIELD

The present invention relates to radiographic imaging systems and, more particularly, to radiographic apparatus having means for producing images derived from radiation shadowgraphs derived with the use of neutron or X-radiation sources.

BACKGROUND ART

The forming and processing of radiographically produced shadowgraphs or radiation transmission patterns to produce visual images of a specimen or workpiece is of interest in various applications, such as the radiographic inspection of various structural components. Previously, such inspection techniques entailed the forming of photoshadowgraphs. A photographic film plate was positioned adjacent an object to be inspected by the neutron or X-ray source, the object being positioned between the film and the source of radiation. When neutron or X-radiation is transmitted through any heterogenous object, it is differentially absorbed, depending upon the varying thickness, density, and chemical composition of the object. The image registered by the emergent rays on a film adjacent to the specimen under examination constitutes a shadowgraph, or radiograph, i.e., an intensity pattern of the rays transmitted, of the interior of the specimen.

X-radiation may be used in industrial applications wherein, for example, it is desired to evaluate a metal casting suspecting of having internal cracks, separations, voids, or other defects; and it is, of course, employed widely in medical applications. X-rays are, in general, substantially more penetrating than neutron radiation with respect to "low-z" materials such as aluminums, plastic, boron, carbon, and the like. Radiographs produced from neutron radiation are employed, for example, when it is desired to form an image of hydrogenous, or organic materials which may be present within metallic sructures. Neutrons penetrate low-thermal-cross-section materials such as lead, aluminum, steel, and titanium, but are absorbed by organic, hydrogenous materials. With respect to metallic structural members, an indication of such hydrogenous materials within the structure may reveal the presence of water, hydroxides, and other corrosion products. Such corrosion may be in the form of intergranular corrosion, with accompanying exfoliation, of materials such as aluminum, and certain other metals. Stresses in aluminum aircraft components, for example, produce internal, intergranular corrosion which is invisible and not accurately imaged by conventional, non-destructive inspection techniques; such corrosion may result in critical failure of major structural elements if it continues undetected. As in the design of load-bearing or structural members for various industrial applications, the conventional design philosophy for aerospace components entails a substantial degree of "over design" for ensuring structural integrity of the components. As will be understood by those in the art, such an excess of material results in correspondingly higher weight and cost, and in lower performance and fuel efficiency than would be obtained if compensation for potential, undetectable internal deterioration was not necessary. Similarly, the permissible useful life of such components is also based upon safety margins which can be substantially reduced if positive assurance were obtainable that internal, or hidden deterioration had not occurred to a significant degree.

Further difficulties with respect to nondestructive testing of aerospace components relate to the possibilities of surface corrosion on internal components hidden from visual inspection. Corrosion which may occur within honeycomb cell structures or panels may result in the separation of honeycomb cores from outer skin surfaces, and the like.

In the past it has been attempted to produce process images produced from low level radiation such as neutron, or low level X-radiation, by exposing photographic films, to the radiation for an appropriate period of time, and developing the film for inspection. The use of photographic film provides the advantage that, through exposure over an extended period of time, very low levels of radiation may form a satisfactory photoradiograph. Exposure times, film speed, radiation levels and film types may be varied. It will be understood, however, that the delays entailed in set-up film processing imparts limitations in inspection efficiency, particularly, when it is desired to inspect, and reinspect, large components, or large numbers of components. For this reason, modern radiographic inspection systems have employed low-light-level television cameras for producing television images derived from the radiation of specimen, whereby a television display corresponding to a radiophotograph is formed. The television monitor may be located in a facility remote from the radiation source, which may afford advantages when hazardous radiation is present. Additionally, television monitoring permits continuous monitoring of a component as real, or "near real time" examination. Such low-light-level television cameras may be of the image orthicon type or of other types such as CID or CCD, and often employ mutliple stages of image intensification or amplification. Modern, low-light-level cameras include various refinements and intensification techniques, such as silicon intensified targets (SIT), secondary electron conduction (SEC), charge-storing, and amplifying.

Two general approaches to the formation of television images of irradiated specimens are illustrated in U.S. Pat. Nos. 3,280,253 and 3,668,396, to R. C. McMaster, et al. and J. A. Asars, et al., respectively, both of which are hereby incorporated by reference. The system of the McMaster patent employs a single stage, camera tube which is sensitive to X-radiation. In use, a radiation source is positioned to direct X-radiation directly toward the television camera tube after transmission through a workpiece to be inspected, and an image is formed on the camera tube target by electrons derived from the X-radiation directed toward the camera, and the image is intensified by the use of periodic beam scanning, in which the radiation builds up adequate image potential (an image pattern comprising a loss of positive charges at portions of a semiconductor target) between raster scanning cycles. A satisfactory TV image is produced by intermittent scanning of the target by the electron beam raster scanner. The McMaster camera includes no intermediate intensifying stages. Such single stage camera tubes provide relatively moderate gain in comparison with highly sensitive tubes such as that disclosed in the recent Asars patent. The thermal neutron radiation, i.e., radiation from which the higher energy neutron and, gamma rays have been removed, as may be obtained from portable radiographic generator systems such as that disclosed in U.S. Pat. No. 4,300,054, issued Nov. 10, 1981, to W. E. Dance, et al., which is incorporated by reference. The system of U.S. Pat. No. 4,300,054 employs a moderator fluid and filter for attenuating the hard, gamma radiation from energy produced by a radiation generator tube. There is a need, particularly in the inspection of aircraft and other components by low power, non-isotopic radiation sources, for an efficient television radiographic display means wherein a high resolution image is produced for convenient viewing.

A problem entailed in prior radiographic systems has been difficulty in producing a high resolution, finely detailed image in the presence of varying levels of radiation. High radiation peaks may tend to overload and blur the camera and may even damage the camera. Another problem has been that very low levels of radiation, such as those obtained from thermal neutron sources and from low level X-rays, have been difficult to record because of inherent system noise. The obtaining of detailed images required to show fissures and details of internal deterioration of metals with sufficient resolution to ensure that no critical faults exist in a piece under inspection is of importance in many applications. A further deficiency in prior inspection systems has been their limitation to undesirably narrow ranges of energy levels. That is, those instruments sensitive to high level radiation such as produced by X-McMaster system may thus be considered to have a relatively high level of input radiation (radiation directly from the X-ray source, which is of generally higher intensity and penetrating potential than portable neutron sources) and a relatively low level of internal intensification or amplification in comparison with multi-stage cameras such as that disclosed in the Asars patent. Such systems are advantageous for certain applications, and such single stage television cameras are less expensive and complex than multi-stage, very low-light-level cameras.

The Asars system employs a phosphor screen to provide a large field of view of appropriate resolution and detail, the phosphor screen serving to generate scintillations of light as the screen receives gamma radiation derived from a neutron source. The light scintillations on the screen are detected and intensified through the sensitive, multi-stage SEC camera tube. To provide adequate light amplification, the camera tube employs several stages of image intensification, including an initial image intensifier tube section and an intermediate image intensifying section. As will be understood by those in the art, sophisticated low-light-level cameras such as that employed in the Asars system are highly complex and expensive.

The present system is intended to provide a radiographic television display with a relatively lower cost and less complex camera system, while at the same time providing very high sensitivity to low radiation levels. In particular, it is intended to provide a radiographic system sensitive to "soft" or radiation have been insensitive and not usable with lower levels of radiation commonly received as neutron radiation. Prior systems were not usable with low-level neutron radiation.

DISCLOSURE OF THE INVENTION

It is, accordingly, a major object of the present invention to provide a new and improved radiographic imaging system.

Another object is to provide such an imaging system which is sensitive to relatively low levels of radiation, including thermal neutron radiation free of any substantial gamma radiation. A still further object is to provide such a system which is operable to produce images of high resolution derives from thermal neutron radiation of, for example, at least about 100 neutrons per square cm. per second and X-rays from very low to very high flux levels.

Yet another object is to provide such an imaging system which is usable to provide high resolution television images, and which can provide such images derived from shadowgraphs produced by both neutron and X-radiation.

A further object is to provide an imaging system for producing a television image which is a combination of images derived from shadowgraphs produced by neutron and X-ray radiation. In this object, the present invention produces a composite image of the workpiece being examined resulting from irradiation of the object by neutron and X-ray radiation.

A further object is to provide such an imaging system in which highly complex, low-light-level television cameras with multiple stages of intensification are not required, yet which provides an overall radiographic sensitivity comparable to or greater than such prior systems.

Another object is to provide such a system in which the television image produced is free of any substantial noise and distortion, wherein highly detailed images may be displayed permitting accurate inspection of components for small cracks, voids, fissures, and other similar faults.

Another object is to provide s superior image in the presence of substantially different flux levels within the same field of view, i.e., to provide "low-bloom" capability.

Another object is to provide such an imaging system which is of practicable, relatively straight-forward and inexpensive construction, permitting convenient portability.

Other objects and advantages will be apparent from the specification and claims and from the accompanying drawings illustrative of the invention.

DETAILED DESCRIPTION

Figure 1:
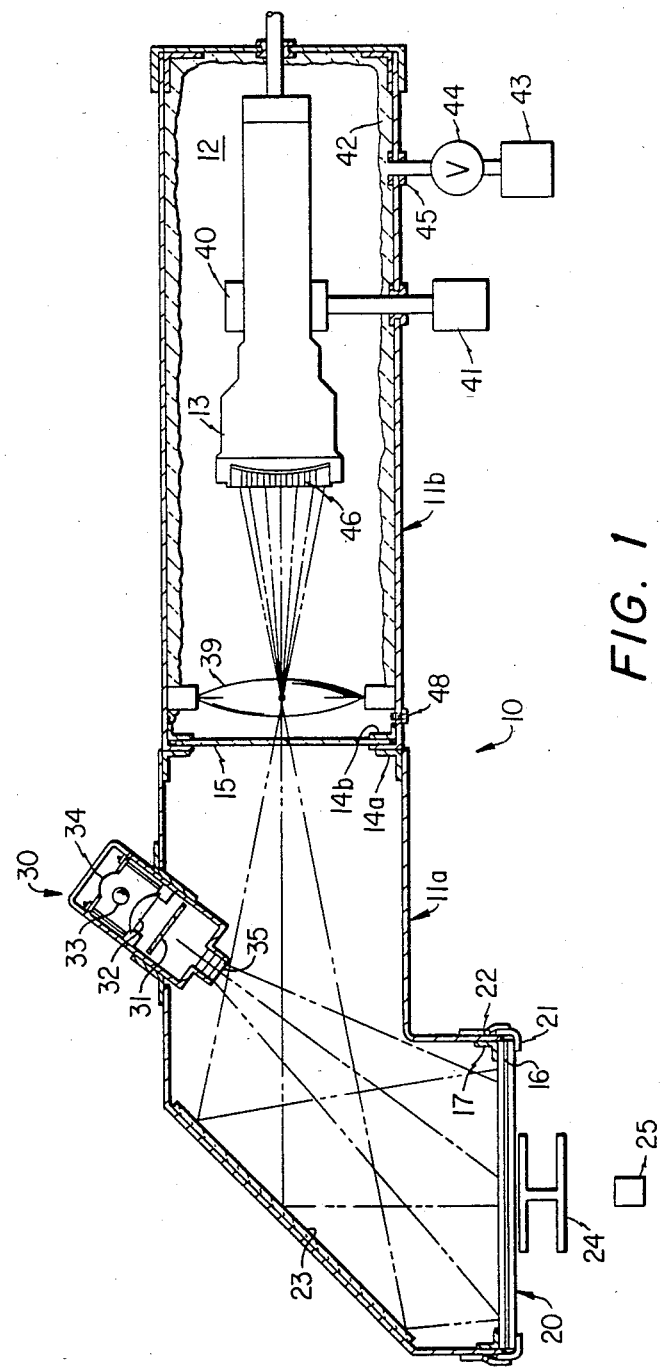
FIG. 1 is a partially diagrammatic, sectional view of the radiographic imaging system.

With initial reference to FIG. 1, radiographic imaging system 10 comprises a housing consisting of first and second segments 11a and 11b. As will be understood more fully from the discussion, the first housing 11a is closed to prevent the entry of light, and the second housing, in addition to being closed, defines a substantially gas impervious chamber 12. The second housing segment 11b is of elongated configuration, and is of a sufficiently large diameter to accommodate a low-light-sensitive television camera 13. Camera 13 is mounted (by internal spiders or other mounting means, not shown) coaxially within the housing segment 11b, and with its optical input screen 46 directioned toward the first housing segment 11a. The camera 13 is a beam scanning camera having a semiconductor target screen, and is suitably of the silicon intensified camera type (SIT); alternatively, other electronic scanning cameras may be employed such as the secondary emission charged coupled device (CCD), or charge injected device (CID) types. An example of a commercially available silicon intensified camera is manufactured by Arvin Diamond Corporation company as Model No. 6073B.

The first and second housing segments 11a, 11b are connected by means such as flanges 14a, 14b affixed within abutting eaves portions of the respective housings, bolted or otherwise connected. A transparent, suitable glass plate 15 is sealingly mounted across an open end of the second housing segment 11b in front of the camera 13 permitting the passage of light to the camera input screen 46, as will be described in more detail hereinbelow. The first housing segment 11a is preferably generally L-shaped, having a perpendicularly facing window 16 at its end opposite the second housing segment 11b.

A flange 17 is mounted peripherally within the opening 16 and a radioluminescent screen structure 20 is fitted within the opening 16 against the internally mounted flange 17. An outer molding frame member 21 is detachably affixed to the housing segment 11a around the opening 16, the housing being suitably provided with latch mechanisms 22 permitting convenient fastening of the frame member 21 against the radioluminescent or phosphorescent imaging screen 20 which in turn is in intimate contact with the internal flange 17, whereby extraneous light is kept from the housing segment 11a. At the end of the housing segment 11a above the opening 16, a mirror 23 is mounted extending along a plane skewed by 45 degrees from the longitudinal axis of the housing and from an axis perpendicular to the plane of the screen structure 20, whereby images produced on the radioluminescent screen 20 are reflected by the mirror along the longitudinal axis of the housings 11a, 11b, and toward the camera 13. A workpiece 24 is positioned closely adjacent the radioluminescent screen 20 between the screen 20 and a source of radiation 25, the source 25 suitably being a source of or thermal neutron radiation, or low level or high level X-radiation, preferably emitted from means as from essentially a point source, for providing as sharp a shadowradiograph as possible upon the radioluminescent screen 20. Preferably, as suggested above, the source 25 may be a non-isotopic, portable neutron generator as disclosed in U.S. Pat. No. 4,300,054, which produces a collimated beam of thermal neutrons directed toward the screen.

A test pattern projector 30 is mounted above the screen within the first housing segment 11a and is directioned to form a projected image upon the inner side of the radioluminescent screen 20. As will be understood from the description of the operation of the system, the system preferably includes such a projection system because at low flux levels, the very low levels of scintillations produced on the screen 20 are not sufficient to permit adjustment of the focus current and target bias voltages during operation of the camera. The test pattern projected on the screen is of sufficient intensity to permit convenient adjustment of both focus current and bias voltage, for subsequent use with the radiation source (without the projected image). The test pattern projector 30 includes a test pattern transparency 31, a condensing lens 32 being positioned between the transparency and a projection lamp 33 positioned in front of a projection mirror 34. Projection lens system 35 is directioned toward the radioluminescent screen 20. The housing of the test pattern projector 30 is removably affixed through an opening formed in the upper portion of the first housing segment 11a by means of a flange structure 36, which may be bolted to the housing.

The television camera 13 is, in the preferred embodiment of the system, cooled to reduce the greatest extent possible any noise. As shown diagrammatically in FIG. 1, the camera 13 is preferably fitted within a cooling ring 40, the cooling ring 40 being mounted circumferentially of the target section of the camera, a will be more fully described hereinbelow with reference to FIG. 2, for maintaining the target preferably at temperatures in the range $-15°$ to $-40°$ C. The cooling ring 40 may comprise an annulus through which cryogenic, liquid nitrogen is circulated from a source, represented at 41, external of the housing segment 11b. Alternatively, the cooling ring 40 may comprise a Peltier junction device powered electrically. The second housing segment 11b is preferably insulated by insulation 42 formed on its inner wall surfaces. The chamber 12 of the second housing segment 11b is preferably maintained as a moisture-free environment to prevent condensation upon the television camera 13, and a lens structure 39 positioned between the television tube input and the glass plate 15, as will be more fully described hereinbelow. For preventing condensation on the camera 13 or lens structure 39, the interior of the second housing segment 11b may be evacuated, or preferably, charged with a drying agent such as nitrogen from source indicated at 43. Suitably, the nitrogen source 43 or other dry nonflammable, electrically insulating gas communicates through valve 44 through tubing conducted through fitting 45 mounted within a suitable opening formed in the wall of the housing segment, and an outlet 48 is incorporated into the opposite end of the housing segment 11b. Prior to use of the system 10, outlet 48 is opened and nitrogen or other gas is permitted to flow through the inlet formed through fitting 45 for a period of time sufficient to remove most of the air and moisture from within the housing chamber 12 and charge the chamber with nitrogen. Subsequently, to pressurize the chamber 12 to approximately 6 psi, after outlet 48 is closed; then valve 44 is closed. It has been found in our experiments that such a charge is sufficient for preventing condensation on the camera 13 and lens structure 39 over an extended period of time of, for example, several months, with no need for further charge.

Figure 2:
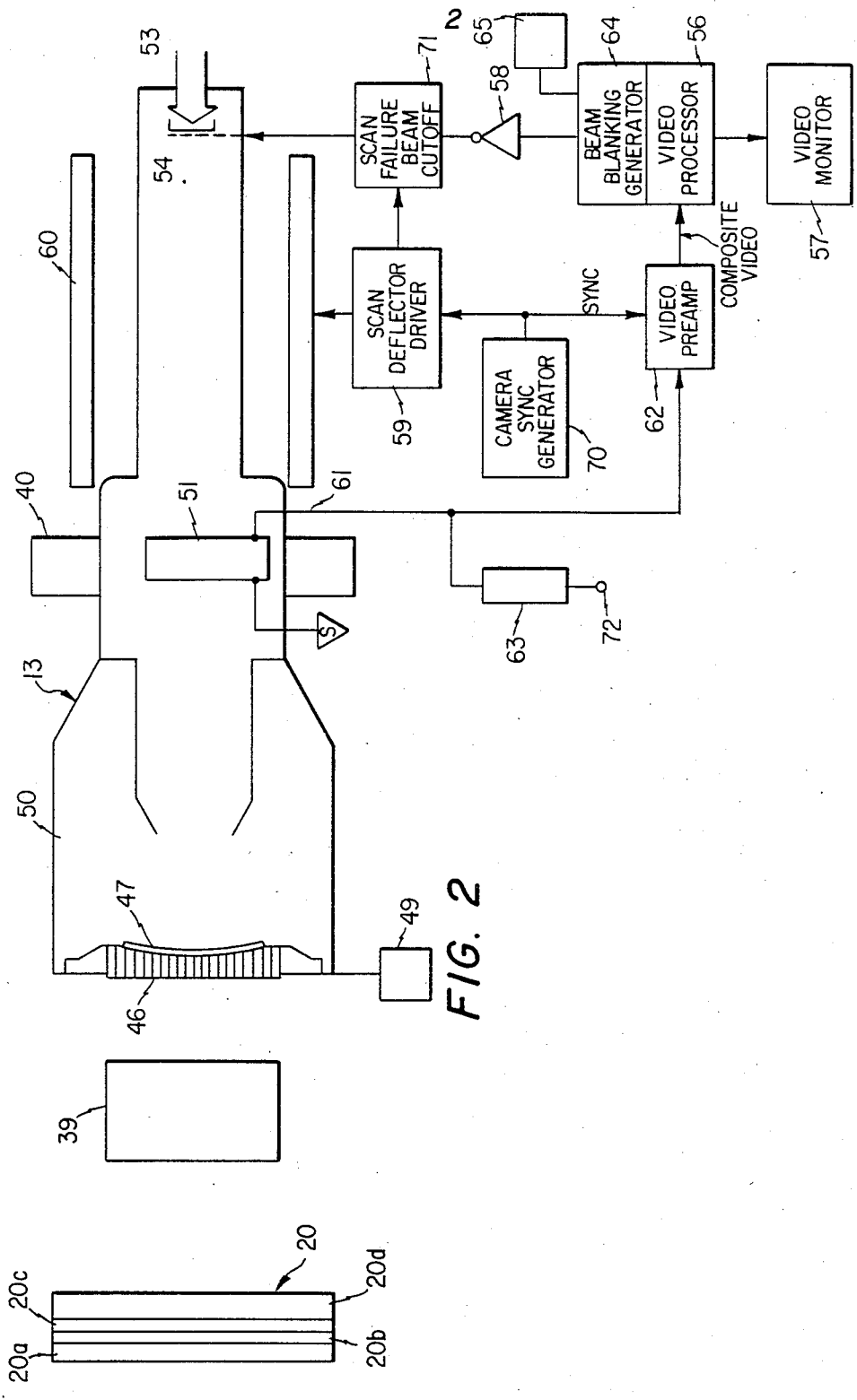
FIG. 2 is a diagrammatic representation of the video tube, in combination with the beam blanking, video processing, and video monitoring circuitry.

With reference now to FIG. 2, the optics and circuitry of the system are shown diagrammatically in somewhat greater detail. An important feature of the invention is the combination of a high output, radioluminescent screen structure 20 with a sensitive, low-noise camera 13 upon which light scintillations are gathered and integrated internally by means of target blanking. It should be understood that, in contrast with prior systems, target blanking is not employed for increasing image intensity, but is instead employed for statistical purposes, i.e., for accumulating sufficient scintillation information to form a radiographic image between electron beam raster scanning of the target to provide an adequate image. The light-emitting, radioluminescent screen structure 20 includes an outer plate 20a of a material as transparent as possible to the radiation employed, but which is opaque to light. It is typically of aluminum, or of another material of a low "Z" number and low thermal neutron absorption characteristics. For convenience, a sealing layer 20b, of aluminum foil, is suitably employed adjacent the aluminum plate 20a to protect the phosphor layer 20c. The phosphor layer 20c is suitably coated or deposited on a substrate 20d, which is of a transparent material such as glass. Alternatively, the phosphor layer 20c can be deposited on the interior surface of the initial, outer plate 20a, with or without a protective glass plate substrate 20d.

The system differs from prior systems in its use of a relatively high-light-output radioluminescent layer 20c on the imaging screen, which permits the use of a relatively lower gain camera 13, and in the integration of scintillations on the target during the blanking periods. Preferably, the phosphor layer consists of a thin layer of a non-radioactive isotope or lithium in lithium fluoride, suitably combined with zinc sulfide, deposited on the substrate. In prior art systems, lithium-based phosphor layers have been used for gross, low resolution imaging purposes, but they inherently produce light scattering and diffusion, when subjected to radiation, which has in the past prevented their use in normal or high resolution imaging. In the present system, the prior difficulties are eliminated by the use of a very thin layer of the material, of about 0.025 inches or less, and preferably of about 0.020 inches or less. The lithium fluoride powder is mixed with a lithium binder material for laying the material in a thin film on the substrate at a nominal thickness of 0.01 inches to 0.02 inches. Suitably the neutron-to-light radiophosphorescent converter material consists of a mixture of lithium fluoride and zinc sulfide powders mixed with a binder material, preferably one which also contains lithium, or is otherwise held in place on the substrate by a thin transparent coating material. It is desirable to limit the quantity of binder materials approximately 10-15% by weight for providing maximum light output. Although various methods are known and utilized for laying materials in a thin film on a substrate, e.g., thin film chromotography, colloidal suspension in a settling tank etc., a recommended method is to form a suspension of the powder mixture in liquid solution containing a small quantity of the binder materials and then, apply the resulting slurry to the substrate by "painting" or loading the substrate with the material, and then drawing a blade or knife-like edge such as a "doctor's bar" across the surface to spread the material uniformly across the substrate. In order to maintain uniform thickness, the substrate must be flat, and rigidly attached to a machined flat surface. Coating thickness can be controlled to within 0.001" using this technique. As previously suggested, thin coatings of, for example, about 0.010 to 0.020 inches have been satisfactory, and preferably 0.012" to 0.025" techniques are employed.

When used with neutron radiation, the neutron particles react with the lithium to produce alpha particles by nuclear conversion of the lithium atom, and the alpha particle reacts with the zinc sulfide to produce a scintillation of light energy. The lithium fluoride component is thus a conversion element, for converting radiation to alpha particles, and the zinc sulphide component is a light producing element for producing light from alpha energy.

The phosphor radioluminescent layer 20c is of importance as a radiation conversion material for converting the radiation received into low level, visible light radiation.

Lens structure 39 is an objective lens structure positioned to form an image of the phosphor layer 20c on the input fiber optic screen 46 of the camera. The camera 13 itself includes a fiber optic based "lens" input screen 47 having a concave, inner photo imaging layer 46, which converts light derived from the scintillations into electron energy which are accelerated through an intensifying section 50 to the camera target 51 by means of an electric potential field. An intensifier high voltage/gain control 49 controls the voltage level on input screen 46 to change the sensitivity of the intensifying section. The target 51 comprises a semiconductor, suitably silicon structure. Cooling ring 40 preferably maintains the target at a low temperature of $-15°$ C. to $-40°$ C., sufficient to minimize background noise and distortion during blanking periods. As is generally known by those in the art, such camera 13 incorporates a beam generating section represented diagrammatically at 53 and typically employs a blanking grid 54 for imparting a blanking bias preventing scanning of the target 51 in the event of failure of the raster scanning circuitry (for the purpose of preventing damage to the target 51 by extended bombardment of a fixed location on the target 51 by the electron beam). The camera assembly typically includes internal circuitry for effecting raster scanning, including the raster generator and scanning circuitry. Such internal raster scanning circuitry is generally operated in response to external synchronizing or triggering signals to provide television scanning of the target by the electron beam. A video or picture processing unit 56, suitably a unit of the type manufactured by the Quantex Corporation as Model No. DS-20, is emloyed for generating timing and synchronization signals, and for storing, processing, and providing playback of video displays. Its output is fed to a video monitor unit 57 for permitting monitoring of images accumulated through integration of one or more successive frames of scanning. An internal timing and control circuit in the beam blanking generator portion 64 of the picture processor 56 generates timing signals, which are logic signals of a selected time period. These signals are fed through a logic driver 58, suitably an open collector, TTL driver employed to increase the power of the blanking signal and invert it prior to its application to the tube scan failure beam cutoff circuit 71 and subsequently to the camera 13. The beam blanking generator portion 64 of the processing circuitry may be adjusted to vary the blanking period. Adjustment is controlled at camera integration control 65. During application of a blanking signal to the grid 54, the electron scanning beam is biased off. During the blanking period, the electron charge is stored in the silicon target in a pattern corresponding to the image which is scintillating on the radiofluorescent screen.

At the completion of the blanking time interval, the electron beam is unbiased and allowed to scan the target surface 51 as steered by the deflection driver 59, including the raster generator, which is typically connected to the deflection yokes 60 external of the tube. The deflection driver 59 is synchronized with an output signal from the camera sync generator 70 which also syncs the storage of video information derived from the target potential output 61. The target output, derived from 61, is amplified by a video preamp unit 62 and fed to the video processor 56. A load resistor 63 connected between the target 51 and a target power supply 72 imparts a bias to the target.

The video processor 56 serves to accumulate frames generated over a period of time during the non-blanking periods and provides an output to the video monitor unit 57 which is of high resolution, sufficient to permit evaluation of finely detailed internal faults in the specimens or components under examination. The image processor thus periodically activates the electron beam generator, reads resulting images, and processes the images for integrating sequential frames and averaging the frames, for improving clarity, and then continually reads out the processed image to the monitor. Typically, the electron scanning beam is blanked for a large portion of the inspection time. For example, the period of image storage may be on the order of 100 times greater than the scanning period; in some, low level radiation inspection, there may be even longer periods of storage relative to the scanning cycle period, depending upon the scintillation output.

The very low levels of energy produced by scintillations on phosphor screens from thermal neutron radiation or low level X-radiation have not been previously employed for the accumulation of statistical information on a semiconductor target during blanking periods, and the low levels of energies presents problems with respect to the biasing and focusing of the camera 13. For this reason, the test pattern projector 30 (FIG. 1) is initially employed for adjusting the bias.

Thus, an important feature of the invention is its ability to store and accumulate statistically significant scintillation information on the target 51 within the camera 13 wherein the electron charge storage pattern builds up on the semiconductor target screen from individual scintillation events over a period of time until a statistically satisfactory image may be scanned, rather than being scanned continuously. This permits the use of a camera 13 which is of relatively inexpensive, rugged construction in comparison with those employing multiple intensification sections, and thereby minimizes noise and distortion which typically results in multiple stages of light intensification. Thus, the combination of the high output phosphor screen with the blanking of the target scanning produces high resolution images with components of moderate cost and complexity. An important advantage of the apparatus is its ability to produce clear images from low levels of radiation and its ability to produce images derived from both X-ray and N-ray sources without changing the internal configuration of the apparatus, that is, without changes of the structure of the phosphor screen or the camera, etc. Extremely clear images are obtained at very low radiation levels. In our experiments, satisfactory high resolution radiographic images have been produced derived from thermal neutrons radiation levels, for example, at least about 100 neutrons per square cm. per second, and with X-radiation of very low and very high levels (e.g., from 40 KEV, at 0.5 ma, at 30 inches, to 10 MEV). Moreover, images are obtained from such various radiation sources without mechanical modification of the camera lens system, or screen.

The test pattern projector 30, in combination with the radioluminescent screen 20 facing inwardly within a closed housing segment 11a, permits accurate, convenient focusing, both mechanically, i.e., by positioning lens 39, relative to the camera 13, and by adjustment of the target bias, and camera electronic focus, prior to actual radiography operations.

As has been described, radiographic system 10 permits the production of clear images from both X-ray and N-ray sources without changing the internal configuration of the apparatus. It has further been found that a composite radiograph can be produced by combining the signals produced from examining an object using neutron radiation with those produced using X-ray radiation. In one embodiment of the invention, the signals are combined by subtracting one from the other to produce a composite radiograph having characteristics of both the radiograph resulting from use of an X-ray radiation source and from a neutron radiation source. It will be understood by those skilled in the art from considering the present invention that varying features of the object being examined may be revealed by adding the results from neutron radiography and X-ray radiography or by adding or subtracting the two using some factor of the signals involved.

Figure 3:
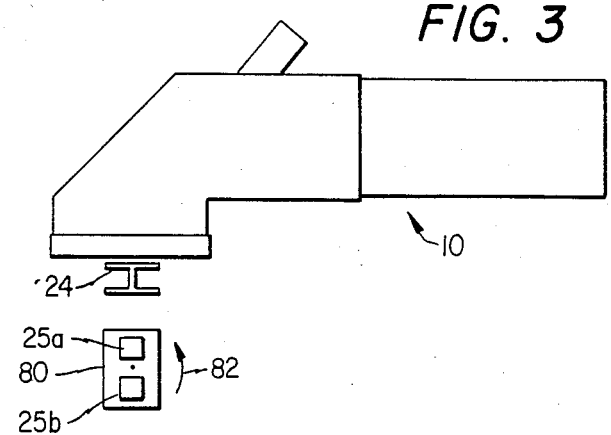
FIGS. 3, 4 and 5 are diagrammatic representations showing the use of both an X-ray and neutron radiation source in conjunction with the radiographic imaging system.
Figure 4:
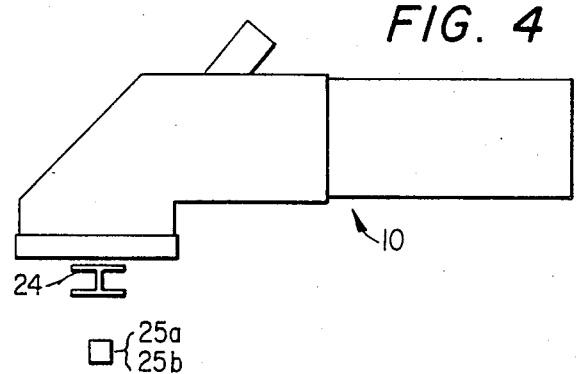
Figure 5:
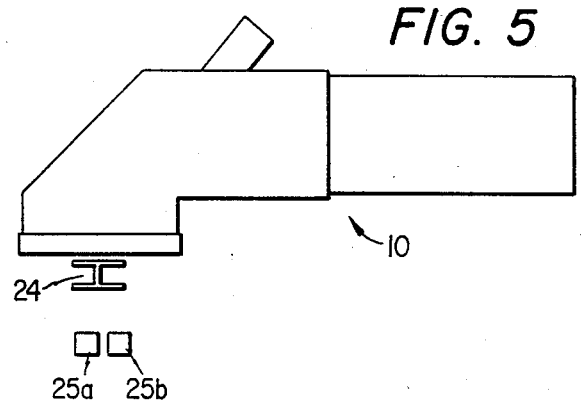

FIGS. 3, 4 and 5 disclose three alternative methods of examining workpiece 24. In FIG. 3, a neutron radiation source 25a, such as the nonisotopic portable neutron generator as disclosed in U.S. Pat. No. 4,300,054, is mounted on a movable platform 80 with an X-ray radiation source 25b. Sources 25a and 25b are used in conjunction with radiographic system 10 to examine workpiece 24. First using neutron radiation source 25a, thermal neutron radiation is directed through workpiece 24 and onto radioluminescent screen 20 (FIG. 1) to produce a scintillation shadowgraph pattern in response to impingement on the screen. Camera 13 has its optical input section directed toward the radioluminescent screen and a charge pattern corresponding to the scintillation patterns produced on the screen are formed on target 51. Television scanning of the target is provided as hereinabove discussed and a video of picture processing unit 56 is employed for generating, timing and synchronization signals and for storing, processing and providing playback of the video displays.

Subsequent thereto, platform 80 is rotated as is indicated by arrow 82 to position X-ray radiation source 25b in position to emit radiation through workpiece 24 and onto radioluminescent imaging screen 20. In the same way as described earlier, picture processing unit 56 stores the image produced as a result of the scintillation pattern produced on the radioluminescent screen and transferred to the target means from which it is scanned. Such output may then be readily combined with that earlier received and stored as a result of examination of the workpiece by neutron radiation. A processing unit of the type manufactured by Quantex Corporation as Model No. DS-20 provides the capability for subtracting one reading from the other to produce a composite picture.

To compensate for the differing levels of intensity between X-ray and N-ray radiation, both the camera integration control 65 and the intensifier high voltage/gain control 49 are used. Camera integration control 65 may be used to vary the beam blanking. Where neutron radiation is used, camera integration control 65 is adjusted for reduced beam blanking as compared to its setting during examination by X-ray radiation. Further, where additional adjustment is required, the sensitivity of optic screen 46 may be adjusted through the intensifier high voltage/gain control 49. By adjusting the high voltage to intensifying section 50, the sensitivity may be adjusted accordingly. Higher voltages are used with neutron radiation examination whereas lower voltage levels, corresponding to lower gains, are used during X-ray radiation examinations. In this way, the radiograph produced using X-ray and N-ray radiation may be adjusted to be compatible for combining to produce a composite radiograph.

In the present invention, both the subtraction of the signal provided by X-ray radiation from that provided by neutron radiation, as well as the reverse subtraction, have been conducted. Each resultant composite image, which may be displayed on video monitor unit 57, provides a valuable visual image of the composition and structural state of the workpiece being examined. Moreover, additional inspection of the workpiece may be conducted by combining the signals produced by use of neutron radiation and X-ray radiation using various weighted factors for two sets of signals.

FIG. 4 illustrates the use of a common source designated as 25a and 25b of neutron radiation and X-ray radiation. Again, workpiece 24 is positioned between the radiation source and radiographic system 10. As described with respect to the arrangement of FIG. 3, radiographic images are produced as a result of the use of neutron radiation and X-ray radiation and combined to produce a composite radiograph. Alternatively, workpiece 24 may be examined by being exposed simultaneously rather than sequentially to the neutron radiation and X-ray radiation. In this embodiment, a composite scintillation pattern is produced on the radioluminescent screen and is transferred to the target of camera 13 for transmittal to a processing unit and then to the video monitor.

FIG. 5 illustrates yet another alternative arrangement where neutron radiation source 25a and X-ray radiation source 25b are positioned side-by-side for either sequential bombardment of the workpiece 24 or simultaneous examination. As in the embodiment illustrated with respect to FIGS. 3 and 4, a composite radiograph is produced as a result of bombardment of the workpiece by both neutron radiation and X-ray radiation.

Although the prior embodiments have disclosed the production of a composite radiograph from the subtraction of signals produced using a neutron radiation source and an X-ray radiation source or alternatively by adding such signals, it will also be apparent to those skilled in the art that one or both of the signals may be factored to produce the most meaningful composite radiograph. For example, one of the signals may be factored in relation to the other of the signals to more clearly depict certain structural features or impediments.

While only one embodiment of the invention, together with modifications thereof, has been described in detail herein and shown in the accompanying drawings, it will be evident that various further modifications are possible in the arrangement and construction of its components without departing from the scope of the invention.

We claim:

1. A radiographic inspection system for producing a shadowgraph or transmission image of an object to be inspected, comprising:

neutron radiation means for selectively directing thermal neutron radiation through the object;

X-ray means for selectively directing X-ray radiation through the object;

a radioluminescent screen structure positioned to receive the neutron radiation and X-ray radiation directed through the object, said screen structure including means for producing a scintillation shadowgraph pattern in response to impingement on said screen structure of radiation directed through the object;

camera means having its optical input section directioned toward said radioluminescent screen for receiving the scintillation shadowgraph pattern and having a target means for forming charge patterns corresponding to the scintillation patterns produced on said radioluminescent screen and scanning means for scanning the target means to generate an optical signal corresponding to the charge pattern formed on the target means; and means for processing signals derived from sequential scans of the target and for combining the signals generated as a result of the exposure of the object to radiation from said neutron radiation means and generated as a result of exposure of the object to radiation from said X-ray means and for producing a television display corresponding to the combination of said signals.

2. The system according to claim 1 further comprising:

means permitting substitution of said neutron radiation means for said X-ray means in said system to expose said object to neutron radiation subsequent to exposure of said object to X-ray radiation.

3. The system according to claim 1 further comprising:

means permitting substitution of said X-ray radiation means in said system to expose said object to X-ray radiation subsequent to exposure of said object to neutron radiation.

4. The system according to claim 1 further comprising:

signal adjustment means for adjusting the magnitude of the output signal from said target.

5. The system according to claim 1 wherein said scanning means comprises a raster scanner.

6. The system according to claim 1 wherein either said neutron radiation means or said X-ray means is first positioned within said system for exposure of said object to said radiation means and wherein said other of the neutron radiation means or X-ray means is substituted for said first radiation means subsequent to the exposure of said object to said first radiation means to expose said object to said other radiation means.

7. The system according to claim 1 wherein said object is sequentially exposed to radiation from said neutron radiation means and said X-ray means and where said signals generated as a result of the exposure of the object to said radiation means are stored and combined to produce a resultant radiograph.

8. A radiographic inspection apparatus for producing an image of an object to be inspected comprising:

radiation source means for directing thermal neutron radiation through the object;

X-ray source means for directing X-ray radiation through the object;

a radioluminescent screen structure positioned to receive the radiation means and X-rays directed through the object, the screen structure including means for producing a scintillation shadowgraph pattern in response to impingement on the screen structure of neutrons and low energy X-rays directed through the object;

a television camera having its optical input section directed toward the radioluminescent screen and having a target means for forming charged patterns corresponding to the scintillation patterns produced on said screen structure, and scanning means scanning said target to generate output signals corresponding to the charge pattern formed on said target by both the radiation source means and said X-ray source means; and means for processing said output signals and for combining said signals and producing a television display corresponding to a combination of said signals.

9. The apparatus according to claim 8 wherein said scanning means comprises a raster scanner.

10. The apparatus according to claim 8 wherein said object is sequentially exposed to radiation from said neutron radiation means and said X-ray means, and where said signals generated as a result of the exposure of the object to said radiation means are stored and combined to produce a resultant radiograph.

11. Radiographic imaging means comprising:
neutron radiation source means for irradiating a workpiece;
means for forming a first image of said workpiece as a result of irradiation by said neutron radiation source means;
X-ray radiation source means for irradiating the workpiece;
means for forming a second image of said workpiece as a result of irradiation by said X-ray radiation source means; and
means for combining said first and second images to produce a composite radiograph of said workpiece.

12. The radiographic imaging means according to claim 11 wherein said first and second images are formed sequentially.

13. The radiographic imaging means according to claim 11 wherein said first and second images are formed simultaneously.

14. A method for producing a radiograph of an object comprising:
irradiating the object using a neutron radiation source means;
forming a first image of said object as a result of said irradiation by the neutron radiation source means;
irradiating said object with an X-ray radiation source means;
forming a second image as a result of irradiation of said object by the X-ray radiation source means; and
combining said first and second images to produce a composite radiograph.

15. The method according to claim 14 wherein said steps of forming said first and second images are performed sequentially.

16. The method according to claim 14 wherein said steps of forming said first and second images are performed simultaneously.

17. The method according to claim 14 wherein said step of forming said first image comprises:
positioning a radioluminescent screen structure to receive the neutron radiation directed through the object and producing a scintillation shadowgraph pattern in response to impingement of radiation on said screen structure directed through the object;
forming a charge pattern on a target within a camera means having its optical input section directed toward the radioluminescent screen, said charge pattern corresponding to the scintillation pattern produced on said radioluminescent screen; and
scanning the target to generate an optical signal corresponding to the charge pattern formed on the target.

18. The method according to claim 17 wherein said step of forming a second image comprises:
positioning a radioluminescent screen structure to receive the X-ray radiation directed through the object and producing a scintillation shadowgraph pattern in response to impingement of radiation on said screen structure directed through the object;
forming a charge pattern on a target within a camera means having its optical input section directed toward the radioluminescent screen, said charge pattern corresponding to the scintillation pattern produced on said radioluminescent screen; and
scanning the target to generate an optical signal corresponding to the charge pattern formed on the target.

19. The method according to claim 18 wherein said step of combining said first and second images comprises:
processing signals derived from scans of the target;
combining the signals generated as a result of the exposure of the object to radiation from the neutron generation means and generated as a result of exposure of the object to radiation from the X-ray means; and
producing a television display corresponding to the combination of the signals.

20. Radiographic imaging means comprising:
neutron radiation source means for irradiating a workpiece;
X-ray radiation source means for irradiating the workpiece;
radioluminescent means for producing a shadowgraphic or transmission scintillation pattern derived from radiation through and around the workpiece;
television camera means having its optical input section directed toward said radioluminescent means and having a target means for forming charge patterns corresponding to the scintillation patterns produced on said radioluminescent screen and scanning means for scanning the target means to generate an optical signal corresponding to the charge pattern formed on the target means; and
means for processing signals derived from scans of the target during the radiation of the workpiece by the neutron radiation means and the X-ray radiation means and for combining the signals generated as a result of the irradiation of the workpiece and for producing a television display corresponding to the combination of said signals.

21. The radiographic imaging means according to claim 20 wherein said means for processing and combining of the signals comprises adding the signals derived from scans of the target during irradiation by the neutron radiation means and the X-ray radiation means.

* * * * *